United States Patent [19]

Sutoris et al.

[11] Patent Number: 5,914,379
[45] Date of Patent: Jun. 22, 1999

[54] COMPRESSION OF ETHYLENICALLY UNSATURATED MONOMERS

[75] Inventors: Heinz Friedrich Sutoris, Frankenthal; Alexander Aumüller, Neustadt; Andreas Koch, Bobenheim-Roxheim; Andreas Deckers, Flomborn; Eckard Schauss, Heuchelheim; Roger Klimesch, Alsbach-Hähnlein; Arend Jouke Kingma, Ludwigshafen; Wilhelm Weber, Neustadt, all of Germany

[73] Assignee: BASF Aktiengesellschaft, Ludwigshafen, Germany

[21] Appl. No.: 09/174,247

[22] Filed: Oct. 16, 1998

Related U.S. Application Data

[62] Division of application No. 08/867,041, Jun. 2, 1997, Pat. No. 5,872,252.

[30] Foreign Application Priority Data

Jun. 5, 1996 [DE] Germany ............................... 19622441

[51] Int. Cl.$^6$ ............................... C08F 2/38; C08F 10/02
[52] U.S. Cl. ........................... 526/204; 526/270; 526/352; 526/318.6; 526/329; 526/331; 526/339; 526/347; 526/348.8
[58] Field of Search ...................................... 526/204, 270, 526/352, 318.6, 329, 331, 339, 347, 348.8

[56] References Cited

U.S. PATENT DOCUMENTS

| | | |
|---|---|---|
| 3,634,346 | 1/1972 | McKeon et al. . |
| 4,016,198 | 4/1977 | Wilder . |
| 4,284,692 | 8/1981 | Rao et al. . |
| 4,665,185 | 5/1987 | Winter et al. . |
| 4,668,721 | 5/1987 | Seltzer et al. . |
| 4,691,015 | 9/1987 | Behrens et al. . |
| 4,912,473 | 3/1990 | Roling . |
| 5,218,116 | 6/1993 | Neri et al. . |
| 5,258,138 | 11/1993 | Gatechair et al. . |
| 5,290,888 | 3/1994 | Gatechair et al. . |
| 5,449,724 | 9/1995 | Moffat et al. . |

FOREIGN PATENT DOCUMENTS

| | | |
|---|---|---|
| 0 178 168 | 4/1986 | European Pat. Off. . |
| WO 96/29311 | 9/1996 | WIPO . |

OTHER PUBLICATIONS

In–House Computer Generated Answer 3 of 6 by Sutoris et al DE 96–19622441–960605 Pages 5 and 6.

*Primary Examiner*—Bernard Lipman
*Assistant Examiner*—N. Sarofim
*Attorney, Agent, or Firm*—Oblon, Spivak, McClelland, Maier & Neustadt, P.C.

[57] ABSTRACT

A process for compressing ethylenically unsaturated monomers at a pressure of 200–5000 bar in the absence of a polymerization initiator comprises carrying out compression in the presence of a sterically hindered amine derivative.

2 Claims, No Drawings

COMPRESSION OF ETHYLENICALLY UNSATURATED MONOMERS

This application is a division of application Ser. No. 08/867,041 filed Jun. 2, 1997 now U.S. Pat. No. 5,872,252.

The present invention relates to a process for compressing ethylenically unsaturated monomers at a pressure of 200–5000 bar in the absence of a polymerization initiator.

The present invention additionally relates to a process for preparing copolymers by such compression and subsequent polymerization, to copolymers obtainable by this process, and to the use of derivatives of sterically hindered amines in a compression process of this kind.

Derivatives of sterically hindered amines have long been known as stabilizers of plastics and of free-radically polymerizable monomers.

EP-A-178 168 discloses a method of inhibiting α,β-ethylenically unsaturated monocarboxylic acids, for example acrylic acid, in the course of their distillative workup.

U.S. Pat. No. 5,449,724 describes a process for preparing thermoplastic ethylene homopolymers and copolymers at from 40 to 500° C. and at 500–5000 bar in the presence of a free-radical initiator and a stable, free radical compound. The presence here of the stable, free radical compound, especially of derivatives of 2,2,6,6-tetramethylpiperidine-N-oxyl, leads to a particularly narrow molecular weight distribution and, associated therewith, to particular physical properties of the polymers.

The compression of ethylenically unsaturated monomers to a high pressure of 500–5000 bar, and in particular the compression of monomer mixtures of ethylene and acrylic acid or acrylic acid derivatives, is frequently accompanied—even prior to the initiation of the polymerization—by instances of premature polymerization in the compressors and precompressors, leading to the formation of deposits and making it necessary to clean the compressors regularly, at short intervals. The use of customary inhibitors, such as mothylhydroquinone and hydroquinone, achieves only a low inhibitory effect for high concentrations of inhibitor.

It is an object of the present invention, therefore, to find a process for compressing ethylenically unsaturated monomers which reduces the formation, during compression, of deposits due to premature polymerization.

We have found that this object is achieved by a process for compressing ethylenically unsaturated monomers at a pressure of 200–5000 bar in the absence of a polymerization initiator, which comprises carrying out compression in the presence of a sterically hindered amine derivative.

In accordance with the novel process, all customary ethylenically unsaturated monomers can be compressed. Examples of suitable monomers are ethylene, propylene, butene and butadiene, vinyl esters of $C_2$–$C_{18}$-alkanecarboxylic acids, such as vinyl acetate and vinyl propionate, $C_2$–$C_{18}$-alkyl esters of acrylic and methacrylic acid, such as methyl, ethyl, propyl, butyl and 2-ethylhexyl acrylate and methacrylate, esters of monoethylenically unsaturated dicarboxylic acids, such as mono- and diesters of maleic and fumaric acid, monoethylenically unsaturated carboxylic acids, such as acrylic, methacrylic, maleic and fumaric acids, amides of monoethylenically unsaturated carboxylic acids, such as acrylamide, methacrylamide, N-mono-($C_1$–$C_{18}$-alkyl)acrylamide, N-mono-($C_1$–$C_{18}$-alkyl)methacrylamide, N-di-($C_1$–$C_{18}$-alkyl)acrylamide and N-di-($C_1$–$C_{18}$-alkyl)methacrylamide, monoethylenically unsaturated alcohols, $C_1$–$C_4$-alkyl vinyl ethers and N-vinyl-heterocyclic compounds, such as N-vinylpyrrolidone, N-vinylcaprolactam and N-vinylimidazoles, and also N-vinylformamide.

The novel process is particularly suitable for compressing monomer mixtures as used for copolymerization. Particularly suitable monomer mixtures are those which in addition to ethylene, propylene, butene or butadiene include the comonomers mentioned above.

Particularly suitable comonomers are derivatives of acrylic or methacrylic acid, and these acids themselves. Examples of suitable derivatives of these acids are the $C_1$–$C_{18}$-alkyl esters, $C_1$–$C_{18}$-mono- and dialkylamides, and the unsubstituted amides. Examples of suitable $C_1$–$C_{18}$-alkyls are methyl, ethyl, n-propyl, isopropyl, n-butyl, isobutyl, sec-butyl, tert-butyl, n-pentyl, isopentyl, sec-pentyl, tert-pentyl, neopentyl and the various isomeric hexyls, heptyls, octyls, nonyls, decyls, undecyls, dodecyls, tridecyls, tetradecyls, pentadecyls, hexadecyls, heptadecyls and octadecyls.

With very particular preference it is possible in accordance with the novel process to compress mixtures of ethylene and acrylic acid and/or methacrylic acid.

In accordance with the invention, the ethylenically unsaturated monomers are compressed in the presence of a sterically hindered amine derivative. The term sterically hindered amines is understood to refer to all secondary amines whose substituents on the carbons adjacent to the amine nitrogen ensure that no hydrogen is present thereon. Preference is given to derivatives of 2,2,6,6-tetramethylpiperidine which are substituted either in position 4 or on the amine nitrogen.

Preferred derivatives of sterically hindered amines are the hyroxylamines. Particularly preferred derivatives of sterically hindered amines are the N-oxyls.

Examples of suitable amine N-oxyls are

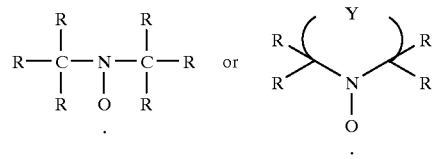

in which each R independently is alkyl, cycloalkyl, aralkyl or aryl, which may also be linked in pairs to form a ring system, and Y is a group required to complete a 5- or 6-membered ring. Examples of R are $C_1$–$C_{20}$-alkyl, especially $C_1$–$C_8$-alkyl, $C_5$- or $C_6$-cycloalkyl, benzyl or phenyl. Y is, for example, alkylene —$(CH_2)_2$— or —$(CH_2)_3$—.

Also suitable are N-oxyl compounds such as

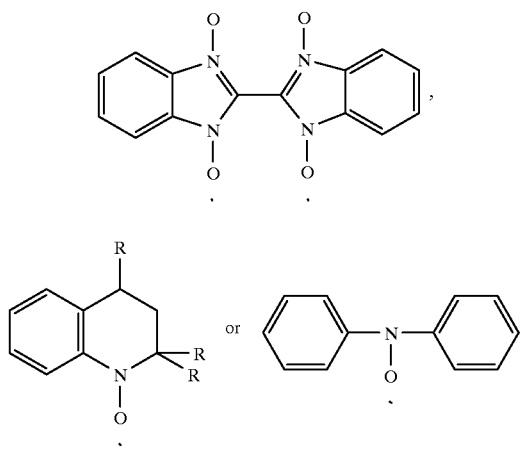

where each aromatic ring may also carry 1 to 3 inert substituents such as, for example, $C_1$–$C_4$-alkyl, $C_1$–$C_4$-alkoxy or cyano.

Preference is given to the use of sterically hindered amine derivatives of cyclic amines, for example of piperidine or pyrrolidine compounds, which in the ring may include a further heteroatom such as nitrogen, oxygen or sulfur, this heteroatom not being adjacent to the hindered amine nitrogen. Steric hindrance is provided by substituents in both vicinal positions to the amine nitrogen, suitable substituents being hydrocarbon radicals which replace all 4 hydrogens of the α—$CH_2$ groups. Examples of possible substituents are phenyl, $C_3$–$C_6$-cycloalkyl, benzyl and, in particular, $C_1$–$C_6$-alkyl, where alkyls attached to the same α carbon atom may also be linked with one another to form a 5- or 6-membered ring. Particular preference is given to the radicals listed individually under $R^1$ and $R^2$. As N-oxyls of sterically hindered amines, preference is given to the use of derivatives of 2,2,6,6-tetraalkylpiperidine.

Preferred N-oxyl compounds in the novel monomer compositions are those of the formula II

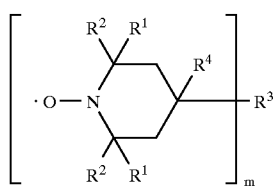

where $R^1$ and $R^2$ are $C_1$–$C_4$-alkyl or phenyl or, together with the carbon to which they are attached, are a 5- or 6-membered saturated hydrocarbon ring, $R^3$ is hydrogen, hydroxyl, amino or an m-valent organic radical attached via oxygen or nitrogen, or, together with $R^4$, is oxygen or a ring structure defined under $R^4$, $R^4$ is hydrogen or $C_1$–$C_{12}$-alkyl or, together with $R^3$, is oxygen or, together with $R^3$ and the carbon to which they are attached, is a ring structure

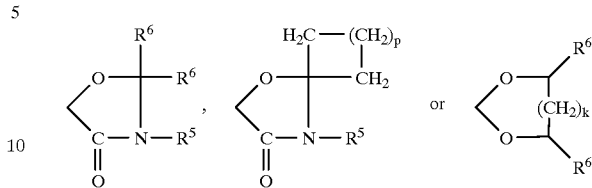

where, if $R^3$ and $R^4$ combine to form a radical, m is 1, $R^5$ is hydrogen, $C_1$–$C_{12}$-alkyl or —$(CH_2)_z$—$COOR^6$, $R^6$ is identical or different $C_1$–$C_{18}$-alkyl, k is 0 or 1, z and p are 1 to 12, and m is 1 to 100.

Examples of $R^1$ and $R^2$ are the $C_1$–$C_4$-alkyls methyl, ethyl, n-propyl, isopropyl, n-butyl, isobutyl, sec-butyl and tert-butyl, or together they may form tetra- or pentamethylene. $R^1$ and $R^2$ are preferably methyls.

Suitable radicals $R^4$ are hydrogen, the abovementioned $C_1$–$C_4$-alkyls, and also pentyl, sec-pentyl, tert-pentyl, neopentyl, hexyl, 2-methylpentyl, heptyl, 2-methylhexyl, octyl, isooctyl, 2-ethylhexyl, nonyl, 2-methylnonyl, isononyl, 2-methyloctyl, decyl, isodecyl, 2-methylnonyl, undecyl, isoundecyl, dodecyl and isododecyl (the designations isooctyl, isononyl and isodecyl are trivial names and derive from the carbonyl compounds obtained by oxo synthesis; cf. Ullmann's Encyclopedia of Industrial Chemistry, 5th Edition, Vol. Al. pages 290–293, and also Vol. A10, pages 284 and 285).

p is preferably 6–12, particularly preferably 9.

z is preferably 1–4, particularly preferably 2.

Examples of $R^5$ other than hydrogen are the abovementioned $C_1$–$C_{12}$-alkyls. $R^5$ is preferably hydrogen, $C_1$–$C_4$-alkyl or $(CH_2)_z$—$COO(C_1$–$C_6$-alkyl), particularly preferably —$CH_2$—$CH_2$—$COO(CH_2)_{11}$—$CH_3$ or —$CH_2$—$CH_2$—$COO(CH_2)_{13}$—$CH_3$.

Examples of $R^6$ include one of the abovementioned $C_1$–$C_{12}$-alkyls and tridecyl, isotridecyl, tetradecyl, pentadecyl, hexadecyl, heptadecyl or octadecyl. Dodecyl and hexadecyl are preferred.

Examples of preferred radicals $R^3$ are the following m-valent radicals

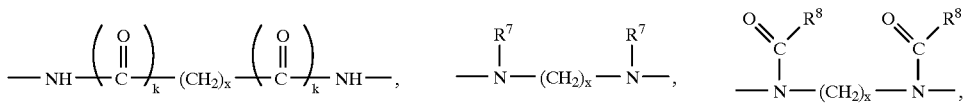

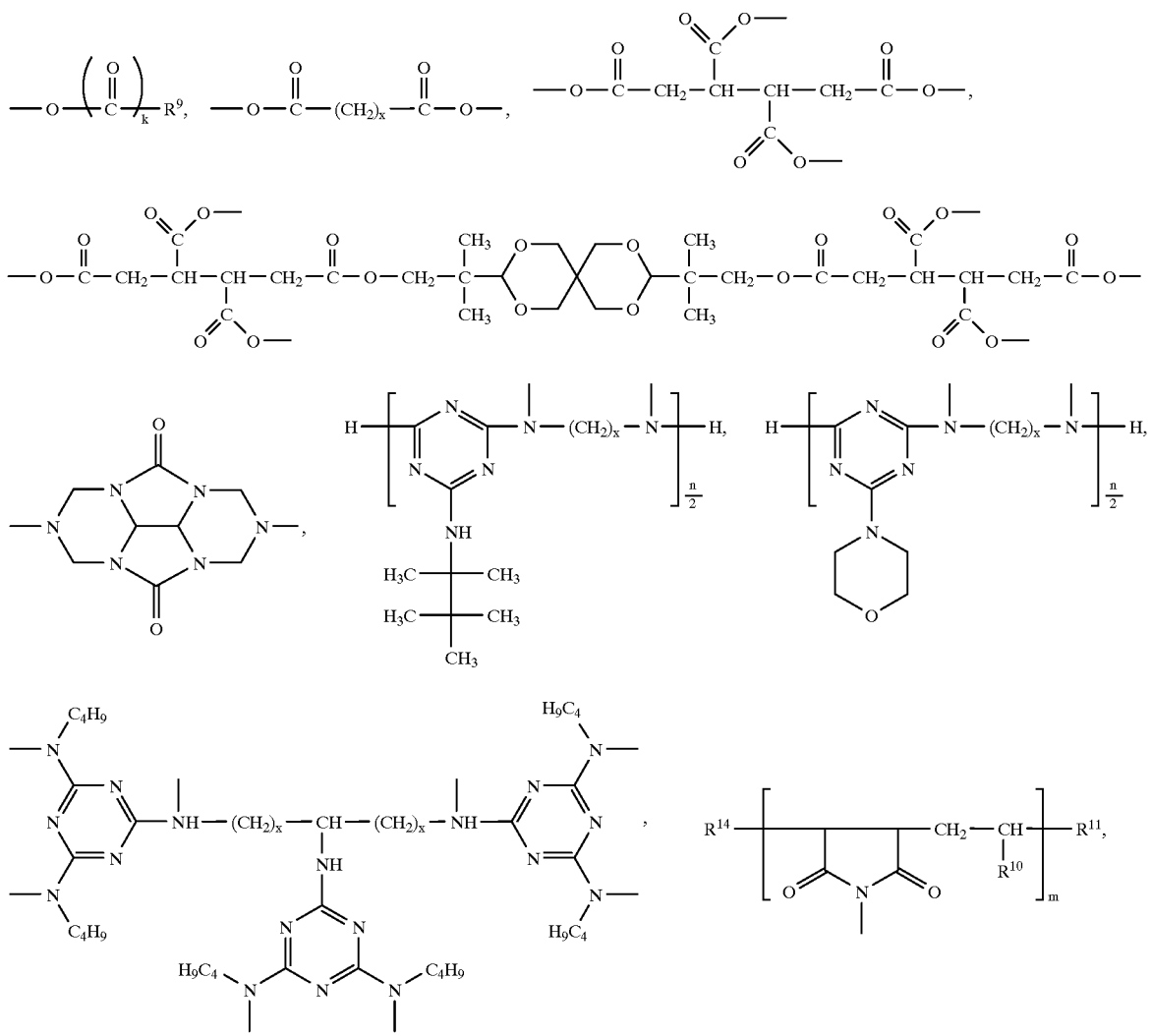

where
- $R^7$ is $C_1$–$C_{12}$-alkyl or —$(CH_2)_z$—$COOR^6$,
- $R^8$ is hydrogen or $C_1$–$C_{18}$-alkyl,
- $R^9$ is $C_1$–$C_{18}$-alkyl, vinyl or isopropenyl,
- $R^{10}$ is $C_8$–$C_{22}$-alkyl,
- $R^{11}$ is hydrogen or an organic radical as usually formed in the free-radical polymerization of the starting monomers,
- k is 0 or 1,
- x is 1 to 12 and
- n is an even number m.

Where $R^3$ is such a radical, $R^4$ is preferably hydrogen. In this case m can be from 1 to 100. m is preferably 1, 2, 3, 4 or a number from 10 to 50, and mixtures are generally employed, particularly in the case of the oligomeric or polymeric radicals $R^3$.

Suitable radicals $R^7$ are the same as specified for $R^5$. $R^7$ is preferably $C_1$–$C_4$-alkyl.

Apart from hydrogen, suitable radicals $R^8$ are the same as those specified for $R^6$. $R^8$ is preferably hydrogen.

Particularly suitable radicals $R^9$ are vinyl, isopropenyl or $C_{15}$–$C_{17}$-alkyls.

Examples of suitable radicals $R^{10}$ are the abovementioned $C_8$–$C_{18}$-alkyls and also nonadecyl, eicosyl, uneicosyl and doeicosyl. In this context, preference is given to mixtures of radicals $R^{10}$ differing in the length of the carbon chain.

$R^{11}$ is hydrogen or an organic radical as obtained in the free-radical polymerization of the initial monomers, in this case an ethylene derivative and a maleimide derivative, ie. a radical, for example, which is formed from the polymerization initiator or from a free radical formed as an intermediate, or from another such radical familiar to the skilled worker.

Other preferred nitroxyl compounds are: 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl (4-tert-butyl)benzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6- tetramethylpiperidin-4-yl) hexahydroterephthalate, N,N'-bis (1-oxyl-2,2,6,6-tetramethylpiperidin-4-yl)adipamide, N-(1-oxyl-2,2,6,6-tetramethylpiperidin-4-yl)caprolactam, N-(1-oxyl-2,2,6,6-tetramethylpiperidin-4-yl)dodecylsuccinimide, 2,4,6-tris[N-butyl-N-(1-oxyl-2,2,6,6,-tetramethylpiperidin-4-yl]-s-triazine, 4,4'-ethylenebis(1-oxyl-2,2,6,6-tetramethylpiperazin-3-one) and tris(2,2,6,6-tetramethyl-1-oxylpiperidin-4-yl) phosphite Particularly preferred N-oxyl derivatives are those of the formula I

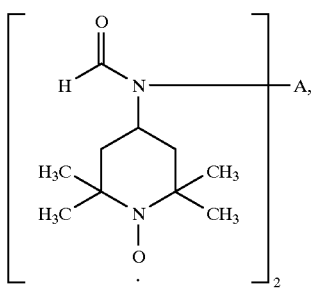

where A is a divalent organic radical of 2 to 20 carbons.

Examples of suitable radicals A are α,ω-alkylenes whose carbon chain can be either straight or branched and can be interrupted by oxygens in ether function, by iminos or by $C_1$–$C_4$-alkyliminos. Such alkylene groups are specified individually, for example, in the earlier German Patent Application 19510184.7. Preferred radicals A are straight-chain α,ω-alkylenes of 2 to 10 carbons; hexamethylene is particularly preferred.

Suitable hydroxylamine derivatives of sterically hindered amines are all those structures which have been mentioned as N-oxyls but where in each case the N-oxyl group is replaced by a hydroxylamino group.

In addition to the derivatives of sterically hindered amines, co-stabilizers can also be used in the novel process. Examples of suitable co-stabilizers are aromatic nitro or nitroso compounds and also hydroxylamines, including those not sterically hindered.

Examples of aromatic nitro compounds which can be used are 1,3-dinitrobenzene, 1,4-dinitrobenzene, 2,6-dinitro-4-methylphenol, 2-nitro-4-methylphenol, 2,4,6-trinitrophenol, 2,4-dinitro-1-naphthol, 2,4-dinitro-6-mothylphonol, 2,4-dinitrochlorbenzene, 2,4-dinitrophenol, 2,4-dinitro-6-sec-butylphenol, 4-cyano-2-nitrophenol and 3-iodo-4-cyano-5-nitrophenol, preferably 2,6-dinitro-4-methylphenol, 2-nitro-4-methylphenol, 2,4-dinitro-6-sec-butylphenol and 2,4-dinitro-6-methylphenol.

Examples of suitable aromatic nitroso compounds are p-nitrosophenol, p-nitroso-o-cresol and p-nitroso-N,N'-diethylaniline.

Other co-stabilizers which can be employed are compounds from the group consisting of the quinones, the phenothiazines and the phenols.

Examples of suitable substituted phenols are: 4-tert-butylpyrocatechol, methoxyhydroquinone, 2,6-di-tertbutyl-4-methylphenol, n-octadecyl β-(3,5-di-tert-butyl-4-hydroxy-phenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tris(3,5-di-tert-butyl-4-hydroxybenzyl) isocyanurate, tris[β-(3,5-di-tert-butyl-4-hydroxyphenyl)propionyloxyethyl] isocyanurate, tris(2,6-dimethyl-3-hydroxy-4-tert-butylbenzyl) isocyanurate and pentaerythritol tetrakis[β-(3,5-ditert-butyl-4-hydroxyphenyl)propionate].

In the novel compression process the sterically hindered amine derivatives are used in a concentration of from 0.00001 to 1% by weight, based on the amount of monomers to be compressed, preferably from 0.0001 to 0.1% by weight. This concentration range is also valid for the cos-tabilizers mentioned.

In accordance with the novel process, the monomers are compressed to a pressure of 200–5000 bar. Compression is preferably carried out in steps, with the final pressure being preferably 1000–4000 bar, particularly preferably 1500–3000 bar.

The compression temperatures are preferably 20–140° C., particularly preferably 30–100° C.

In accordance with the invention, no polymerization initiator is present during compression. In this context, polymerization initiators are all compounds added to the monomers to initiate free-radical polymerization, such as azo compounds, organic peroxides and hydroperoxides. For the purposes of the invention, any oxygen present in the compression mixture is not to be considered as constituting a polymerization initiator.

The novel compression process is preferably part of a high-pressure copolymerization process which comprises compressing the comonomers, individually or as mixtures, in accordance with the novel process and then carrying out polymerization at from 50 to 350° C. by adding a polymerization initiator.

The preferred polymerization temperature is from 150 to 300° C. and the preferred pressure 1000–4000 bar, particularly preferably 2000–3000 bar.

Polymerization can take place by conventional methods, in tube reactors or in autoclave reactors, for example. Any customary additive—molecular weight regulators, solvents, etc., for example—may be present in the polymerization mixture.

The advantage of this novel polymerization process is not only in the longer running times of the compression apparatus but also in an improvement in the polymerization products. For example, in the copolymerization of ethylene with acrylic acid, the latter monomer in particular has a tendency to undergo premature polymerization in the course of compression. This leads to proportions, or at least regions, of acrylic acid homopolymer within the copolymers, and is therefore detrimental to the homogeneity of the product and to the reproducibility of the process. The copolymers obtainable by the novel process, on the other hand, are of relatively high homogeneity.

EXAMPLES

In a precompressor, ethylene was compressed to a pressure of 220 bar. Over 60 minutes, 85 l of a mixture of acrylic acid and isodecane (1:1 by volume), in which the amounts indicated in the table of the stabilizer N,N'-bis-(2,2,6,6-tetramethylpiperidin-1-oxyl-4-yl)-N,N'-bisformylhexamethylenediamine had been dissolved, were pumped into the compressed gas stream (1400 kg/h). The mixture was compressed to 2300 bar in a post-compressor and was transferred continuously to a 35 l steel flow-through autoclave. Polymerization was initiated by adding 0.0025 mol % (based on the overall molar amount of monomers) of tert-butyl perpivalate. The reaction temperature was 220° C. The reaction was at an end when the amount of leakage gas caused by deposits on the post-compressor exceeded 50 kg/h.

The results of the exemplary experiments are shown in the following table:

| Example | Inhibitor conc. [% by wt.] | Running time [h] |
|---|---|---|
| 1 | 0.020 | >168 |
| 2 | 0.010 | >168 |
| 3 | 0.005 | 124 |
| Comparison | 0 | 27 |

We claim:

1. A process for preparing a copolymer from ethylenically unsaturated comonomers, comprising:

compressing said comonomers of said copolymer, individually or in admixture, at a pressure of 200–5000 bar in the absence of a polymerization initiator in the presence of a sterically hindered amine derivative; and polymerizing the monomers at a temperature of 50 to 350° C. in the presence of added polymerization initiator.

2. A copolymer prepared by the process of claim 1.

* * * * *